United States Patent [19]
Bush et al.

[11] Patent Number: 5,249,574
[45] Date of Patent: * Oct. 5, 1993

[54] IMPLANTATION OF LEADS

[75] Inventors: Mary E. Bush, Fremont; Eric S. Fain, Menlo Park, both of Calif.

[73] Assignee: Ventritex, Inc., Sunnyvale, Calif.

[ * ] Notice: The portion of the term of this patent subsequent to Jul. 7, 2009 has been disclaimed.

[21] Appl. No.: 812,427

[22] Filed: Dec. 23, 1991

Related U.S. Application Data

[63] Continuation-in-part of Ser. No. 641,500, Jan. 15, 1991, Pat. No. 5,127,421.

[51] Int. Cl.$^5$ .............................................. A61N 1/05
[52] U.S. Cl. ...................................... 607/9; 128/898; 607/126
[58] Field of Search ...................... 128/785, 419 P, 898

[56] References Cited

U.S. PATENT DOCUMENTS

| | | | |
|---|---|---|---|
| 3,171,132 | 3/1965 | Dritz . | |
| 3,250,450 | 5/1966 | Le Page et al. . | |
| 3,999,555 | 12/1976 | Person | 128/419 P |
| 4,270,549 | 6/1981 | Heilman | 128/784 |
| 4,548,203 | 10/1985 | Tacker, Jr. et al. | 128/419 D |
| 4,821,723 | 4/1989 | Baker, Jr. et al. | 128/419 D |
| 4,865,037 | 9/1989 | Chin et al. | 128/419 D |
| 4,884,567 | 12/1989 | Elliott et al. | 128/303 R |
| 4,938,231 | 7/1990 | Milijasevic et al. | 128/784 |
| 4,946,457 | 8/1990 | Elliott | 606/1 |
| 5,127,421 | 7/1992 | Bush et al. | 128/785 |

OTHER PUBLICATIONS

Brochure by the Dritz Corporation-one page.
Article by Dixon et al. from Laboratory Investigation-Defibrillation, vol. 76, No. 5, Nov., 1987, pp. 1176-1184 Entitled: Improved Defibrillation Thresholds With Large Contoured Epicardial Electrodes and Biphasic Waveforms.

Primary Examiner—William E. Kamm
Assistant Examiner—Scott M. Getzow
Attorney, Agent, or Firm—Steven M. Mitchell; Mark J. Meltzer

[57] ABSTRACT

A lead or other member may be implanted into the body, and typically at the heart, by a method which comprises and following: inserting one of a pair of pivotally attached jaws of an attachment tool through a hole in a body membrane, particularly the parietal pericardium surrounding the pericardial cavity. The other of the pivotally related jaws is placed outside of the body membrane in a position of registry with the first of the jaws. The jaws carry an attachment member which is to be attached for securance to the body membrane. The jaws are brought together in pressing relation with the membrane and attachment member positioned between the jaws, to cause attachment of the attachment member to the membrane. The lead may be pre-attached, or subsequently attached, to the attachment member after the above process steps.

16 Claims, 6 Drawing Sheets

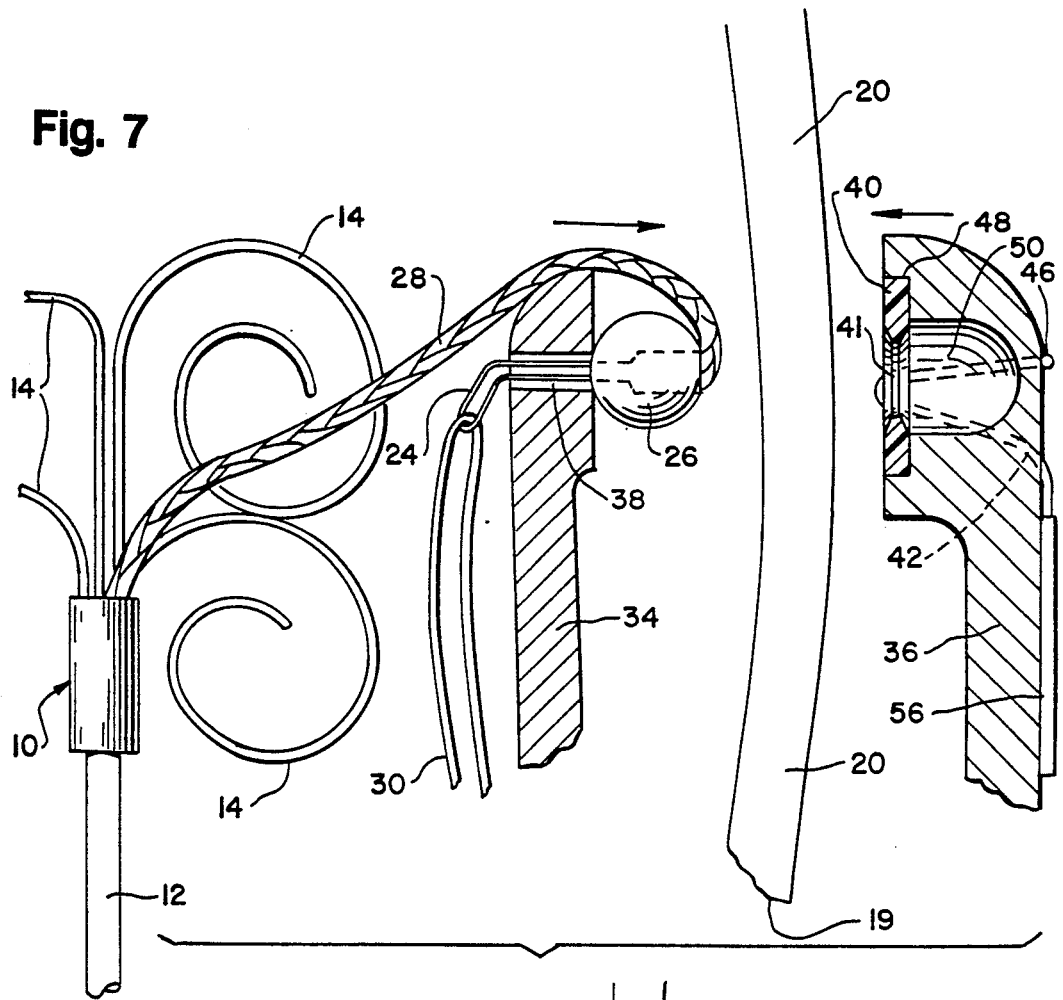
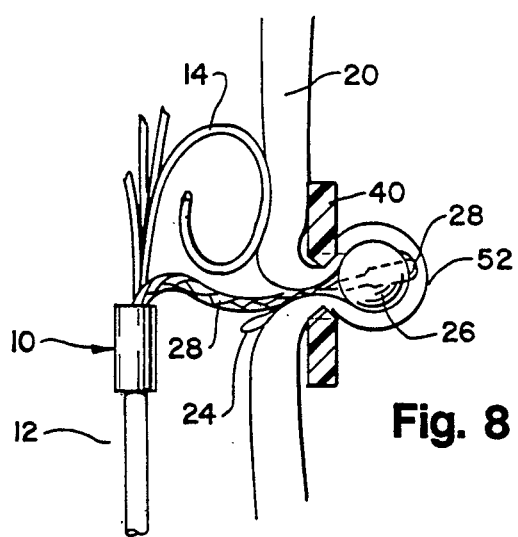

Fig. 9
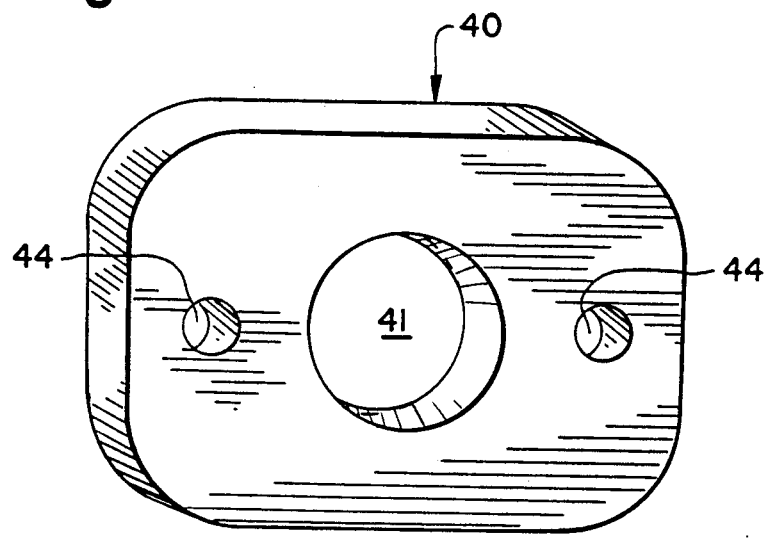
Fig. 10
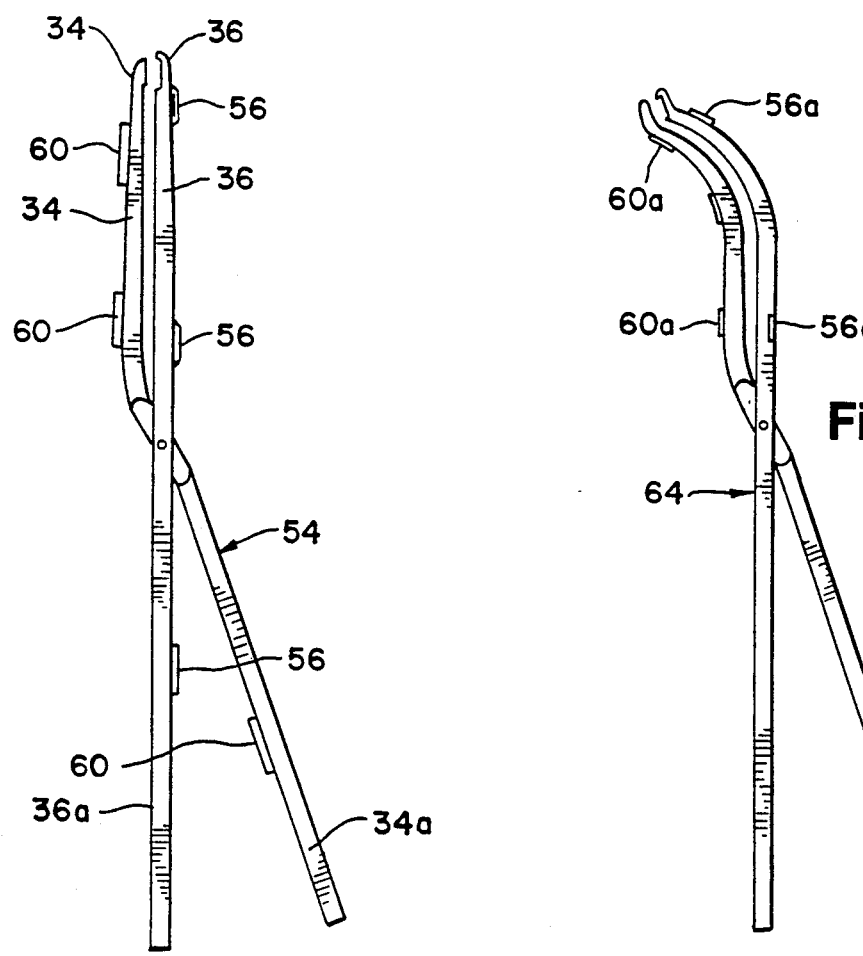
Fig. 11

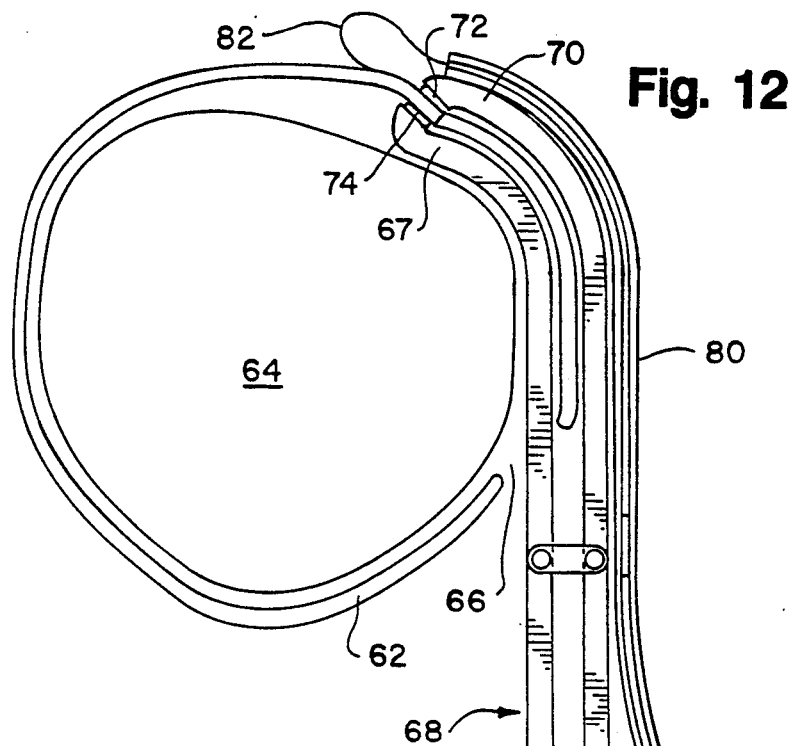
Fig. 12
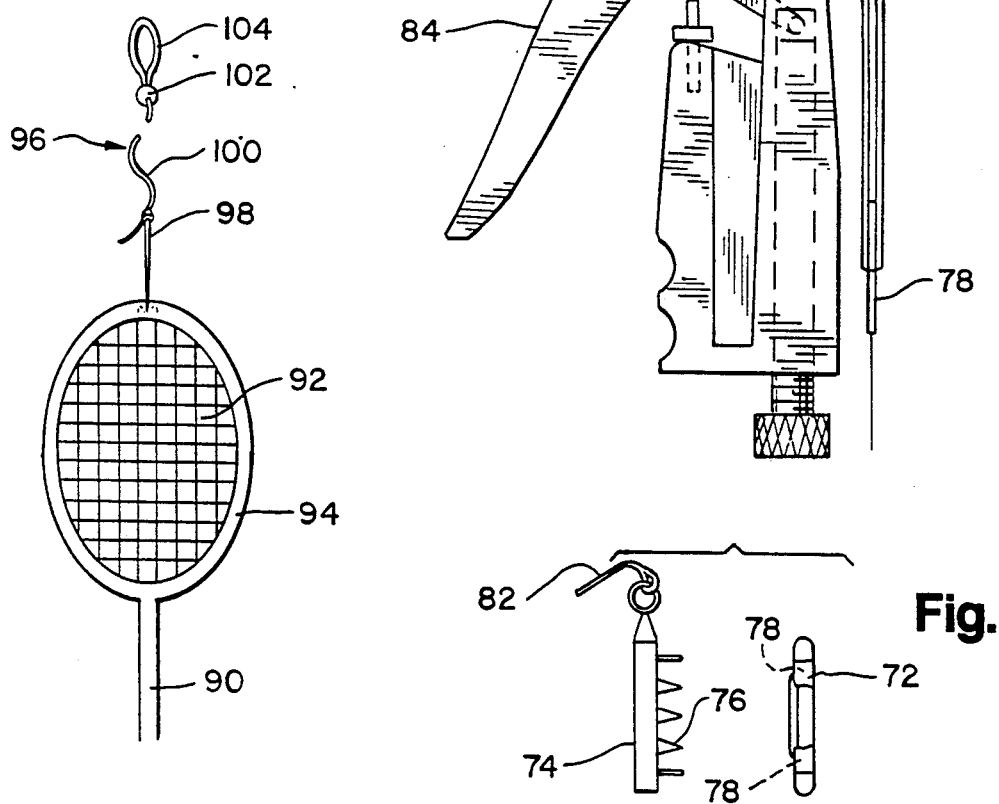
Fig. 14
Fig. 13

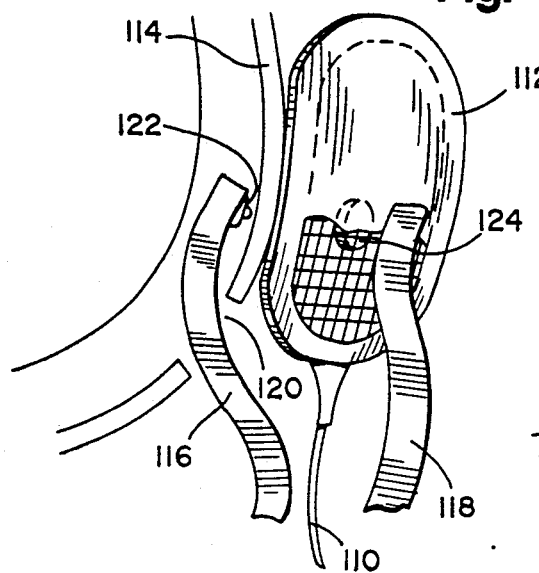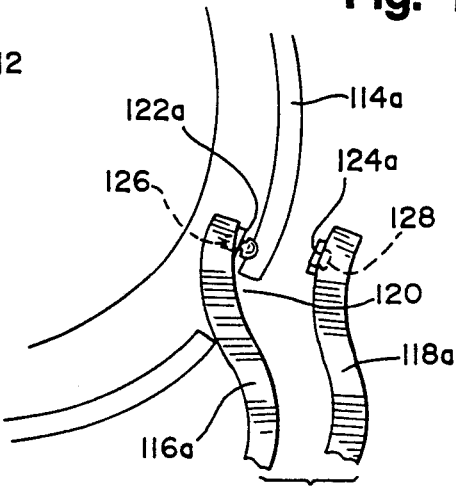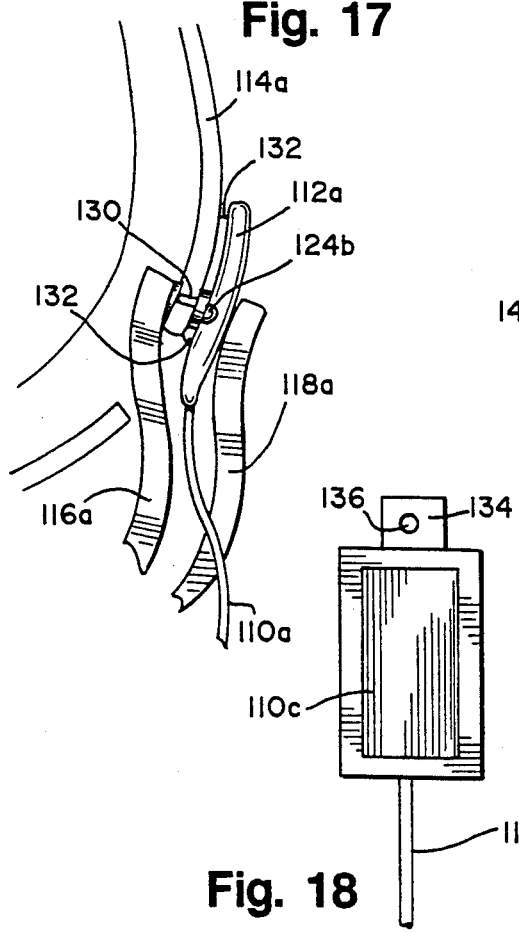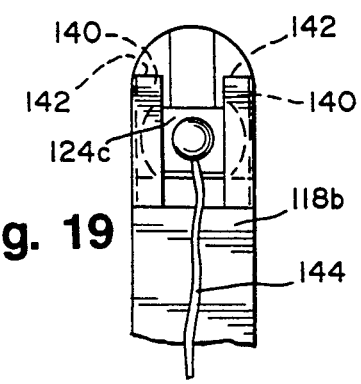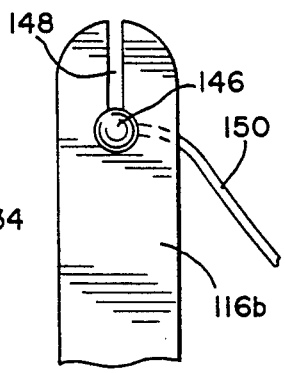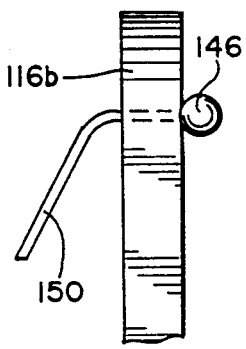

IMPLANTATION OF LEADS

CROSS REFERENCE TO RELATED CASE

This is a continuation-in-part of application Ser. No. 641,500, filed Jan. 15, 1991, now U.S. Pat. No. 5,127,421.

BACKGROUND OF THE INVENTION

This invention relates to a method and apparatus for permanently implanting leads adjacent the heart, plus fixation devices for holding implanted leads in desired positions anywhere in the body. The term "leads" is intended to also include other implantable fixtures besides electrical leads, such as fluid conduits, reservoirs and the like.

It is well-known in the field of cardiology that ventricular fibrillation can be effectively treated by the application of electrical shocks to the heart. Such defibrillation may be achieved by the application of electrical paddles to the chest of the patient or directly to the heart tissue, if the chest is open during surgery.

More recent improvements have lead to the development of implantable defibrillators, which monitor the heart for arrhythmias and automatically initiate defibrillation when fibrillation occurs. Such devices often incorporate electrodes that are located on the epicardium or parietal pericardium, being connected to a defibrillation unit by means of a lead.

However, major surgery is generally necessary to implant and affix present defibrillator lead systems into their desired position. For example, a median sternotomy or lateral thoracotomy may be required. Such procedures can be very traumatic to the patient, and may have adverse side effects such as surgical complications, morbidity, or even mortality. Candidates for such a procedure thus may include only those persons for whom the potential benefits outweigh the significant risks. Because of the significant surgical risks of the present lead systems, many patients who might otherwise benefit from the use of an implantable defibrillator are excluded.

The issue of fixation of the lead into a desired position can be important for any implantable device, but it is especially important for defibrillator leads, since the electrodes of the typical pair of defibrillator leads present cannot be allowed to touch each other. When implanting paddle electrodes via sternotomy or thoracotomy, there is adequate access of the leads and surrounding tissues to suture the edges of the leads to those tissues to fixate the leads in place. However, in the case of a deployable lead that has been placed through a small incision, or a paddle electrode placed through a small incision using a limited surgery technique, suturing by hand is not possible due to the lack of access and the lack of visibility. A deployable lead is a lead that is inserted into its position in a transversely collapsed configuration, with the electrodes being then allowed to expand outwardly into a new, laterally expanded configuration which is typically larger than the incision providing entry of the lead into its desired position.

Another difficulty involved in fixating leads to the epicardium, when compared to fixating leads to the endocardium, relates to the lack of trabeculae for engagement with tines, and also the presence of coronary blood vessels that must be avoided if one attempts to use screws or hooks that penetrate the tissue.

By this invention, a lead is preferably attached to the parietal pericardium, and not the epicardium. Thus there is practically no possibility of rupturing coronary vessels or of tearing myocardium. Also, no endoscope, rigid or flexible, is required in order to provide good fixation of the lead to the parietal pericardium. It is possible to crimp a fixation device as described herein so that no sharp edges of the device are exposed to tissue. Likewise, the fixation device may be visible on x-ray and fluoroscopy, for effective observation both during implantation and afterward. Likewise, fixation devices as described herein may be attached firmly, yet relatively atraumatically, since only fibrous tissue is penetrated and gripped. Thus there is essentially no possibility of puncturing the pleura, and the pericardium remains intact.

The lead may be removed by coring the parietal pericardium, or the lead may be removed by snapping its fixation device apart, while the lead is held by snapping the fixation device together. Also, the fixation device for the lead can be made so unobtrusive that an abandoned fastener can be left attached to the parietal pericardium and a new one placed, if desired.

Thus, the invention of this application exhibits significant advantages over prior art methods for implanting leads, particularly adjacent the heart, as shown for example in Chin et al. U.S. Pat. No. 4,865,037 or Person U.S. Pat. No. 3,999,555, for example.

DESCRIPTION OF THE INVENTION

In accordance with this invention a method is provided for implanting a fastener onto tissue and specifically a lead at the heart, which comprises the following steps:

One inserts a first of a pair of pivotally attached jaws of an attachment tool through a hole in a tissue membrane such as the parietal pericardium surrounding the pericardial cavity, while placing the other of said pivotally attached jaws outside of the parietal pericardium or other tissue membrane in a position of registry with the first of the jaws. The jaws typically carry an attachment member which is adapted for securance to the parietal pericardium or other tissue, and which is typically attached to a lead, for example an electrically conductive lead, or if desired, a tubular conduit lead for the administration of medication or other fluids, or for drainage from areas adjacent to the tissue membrane.

One then brings the jaws together in pressing relation, with the parietal pericardium (or other tissue membrane) and the attachment member positioned between the jaws, to cause attachment of the attachment member to the parietal pericardium or other membrane.

Following this, one disconnects the jaws from the attachment member, and withdraws the jaws.

In some embodiments, each of the jaws may carry an interconnecting portion of the attachment member, with each interconnecting portion being proportioned for mating engagement with the other portion upon the application of pressure of the jaws, with the interconnecting portions and the parietal pericardium or other membrane being positioned between the jaws. The lead, when present, may connect with the attachment member at a position either inside or outside of the parietal pericardium or other membrane.

As another embodiment, a lead or the like may be attached to the attachment member after the attachment member has been placed onto the parietal pericardium or other body membrane. This attachment can take place either before or after disconnection of the jaws from the attachment member.

The attachment member, or interlocking attachment member halves, may be releasably seated in a longitudinal slot which is defined in one or both of the jaws of the attachment tool. The longitudinal slot or slots may be open at their distal ends, so that the attachment member or halves thereof may be retained by the slots against motion transverse of the jaws, but when the jaws are withdrawn, the attachment member or its halves may slide distally out of the slot to remain in the desired position.

In an additional embodiment, an attachment member, connected to tether means, may be inserted through an access site into the body and into the vicinity of the heart or other organ. The attachment member may then be attached to the parietal pericardium or other body membrane, while the tether means extends from the attachment member and through the body to the access site of the patient. One can then slide a lead, or other implantable medical device, along the tether means, beginning at the access site, through the patient to cause the distal end of the lead to occupy a position adjacent to the attachment member. Thus the tether acts rather like a catheter guidewire in facilitating the advancement of a lead, or other medical device such as a catheter, to advance to a desired, predetermined position.

The step of attaching a lead to a fastener member may take place during manufacture, or before the surgical procedure begins, or during the surgical procedure.

The lead used in the method of this invention may be of essentially collapsed outer diameter while placed through the hole in the parietal pericardium or other membrane. Then, after such placement, portions of the lead may be laterally deployed outwardly within the pericardial cavity. Examples of such outwardly deployable leads are well known and of various types. The essentially collapsed outer diameter may be provided in conventional manner by a sleeve outside of a curved electrode or electrodes to hold then straight and inwardly collapsed until the sleeve is removed at which time the electrode assumes a new configuration having an enlarged lateral dimension, as shown, for example in the cited Chin et al. U.S. Pat. No. 4,865,037 and other prior art. See also Bush et al. application Ser. No. 591,389, filed Oct. 1, 1990.

The tool used in accordance with this invention for securing leads to a tissue site may comprise a pair of opposed, movable jaws for applying compressive action to join together first and second engaging parts of the attachment means, which parts are each respectively and releasably carried on one of the jaws in opposed relation. Such a tool may be generally conventionally manufactured to accomplish this purpose, except as otherwise described herein.

Preferably the first and second engaging parts of the attachment means are of the interlocking variety so that they may be brought together by the jaws, with a body organ portion such as the parietal pericardium positioned between them, for releasable or permanent interlocking engagement. One of the first and second parts of the attachment means may then be attached to a lead, so that the lead is secured to the body organ by this action.

Among other designs, the first part of the attachment means may comprise a bead while the second part of the attachment means may comprise a plate having a first aperture. The first aperture is sized to allow the bead to be pressed through the aperture in snap-fit relation by the compressive action between the opposed jaws.

The plate is preferably made of a semi-flexible material having a desired amount of resilience, so that the snap-fit relation may be achieved with relative ease, yet the retention will be strong enough for the desired purposes.

DESCRIPTION OF THE DRAWINGS

FIG. 7 is a detailed, elevational view, taken partly schematically, illustrating substantially the step of FIG. 5 in greater detail;

FIG. 8 shows details of a step subsequent to the step of FIG. 7;

FIG. 9 is an enlarged, perspective view of the plate which may serve as one of the engaging parts of the fastener member used in this invention;

FIGS. 10 and 11 are plan views of various designs of attachment tools which may be used in accordance with this invention;

FIG. 12 illustrates another embodiment of the implantation of a lead in accordance with this invention, in which the lead is positioned outside of the parietal pericardium and is secured thereto;

FIG. 13 provides a detailed view of the engaging parts of the fastener member used in FIG. 12;

FIG. 14 is a plan view showing how an attachment loop and fastener may be attached to a lead, particularly a paddle electrode, for use in accordance with this invention;

FIG. 15 is a perspective view showing how a lead may be attached to the parietal pericardium by attachment to an attachment member part, which attachment member part is carried by one of a pair of jaws of an attachment tool;

FIG. 16 is a generally schematic, elevational view showing a pair of jaws applying a two-part attachment member to the parietal pericardium;

FIG. 17 shows a step subsequent to that of FIG. 16, where the pair of jaws apply a patch electrode on the outside of the parietal pericardium to the mounted attachment member;

FIG. 18 is a plan view of a patch type electrode which carries a distal tab, with a connector member for connection with an attachment member carried on a body membrane such as the parietal pericardium;

FIG. 19 is an enlarged, plan view of the surface of the distal end of a jaw of an attachment tool, showing how an attachment member or part thereof can be held therein;

FIGS. 20 and 21 are an enlarged, elevational views, taken 90° from each other, showing how a ball-type attachment member part, having an attached cord, can be retained by the jaw in a slot thereof;

DESCRIPTION OF SPECIFIC EMBODIMENTS

Figure 1:
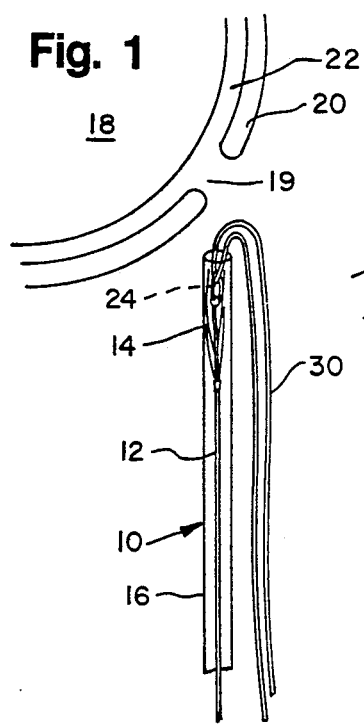
FIGS. 1 through 6 are schematic views of various sequential steps in the method of implanting and affixing a defibrillation electrode lead into the pericardial cavity by attachment to the parietal pericardium.

Referring to the drawings, FIGS. 1 through 6 disclose various steps in the method of implanting a lead at the heart, with FIGS. 7 and 8 showing details of the process. As shown in FIG. 1, a lead 10 comprises a lead body 12 having outwardly deployable electrodes 14, which may be made of conductive metal. Lead body 12 and electrodes 14 are initially closed in an outer sheath 16, typically in a manner as disclosed in Bush et al. U.S. application Ser. No. 591,389, filed Oct. 1, 1990 and entitled Multiple Electrode Deployable Lead. Otherwise, any lead having outwardly deployable electrodes may be used in this particular embodiment, with the electrodes being held in essentially radially collapsed configuration either by a sleeve or by one or more stylets.

Heart 18 of a patient is exposed by a surgical procedure, and an aperture is formed in the parietal pericardium 20, so that access to the pericardial cavity 22 is provided to lead 10.

As one modification to customary deployable electrode leads of the prior art, lead 12 used herein carries a distally mounted loop 24 of nylon suture material or the like. A magnified view of the distal end of lead 10 is shown in FIG. 7. There, loop 24 is shown being connected to a bead 26 which may be made of plastic, ceramic or metal, and which comprises one of the engaging parts of the fastening member used in this particular embodiment, as previously described. Bead 26 is connected to the distal end of lead 10 by a flexible member 28, typically a piece of multistrand cord or the like for permanent securance of bead 26 to the distal end of lead 12. Also in FIG. 7, electrodes 14 are shown in their outwardly deployed configuration after removal of sheath 16, particularly as shown in FIG. 3.

A suture cord 30 is provided, extending along the length of lead 10 and passing through loop 24, with the cord then extending rearwardly again along the length of lead 10. Typically, cord 30 is more than double the length of lead 10 so that both of its rear ends extend out of the incision site and the skin during the surgical procedure.

Figure 2:
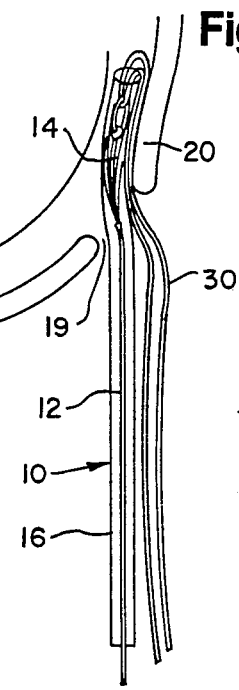

After the aperture 19 has been made in the parietal pericardium 20, the sheathed lead 10, and cord 30 are advanced through such aperture as shown in FIG. 2, until the electrodes 14 of the lead are positioned in the desired spot.

Figure 3:
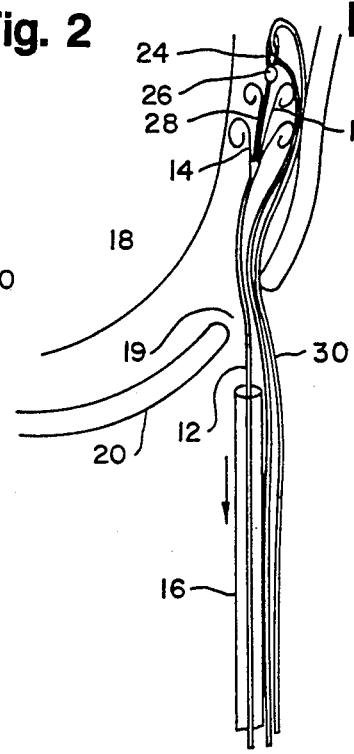

After such positioning takes place, as shown in FIG. 3, sheath or sleeve 16 may be withdrawn. This allows spring electrodes 14 to deploy outwardly as shown.

Figure 4:
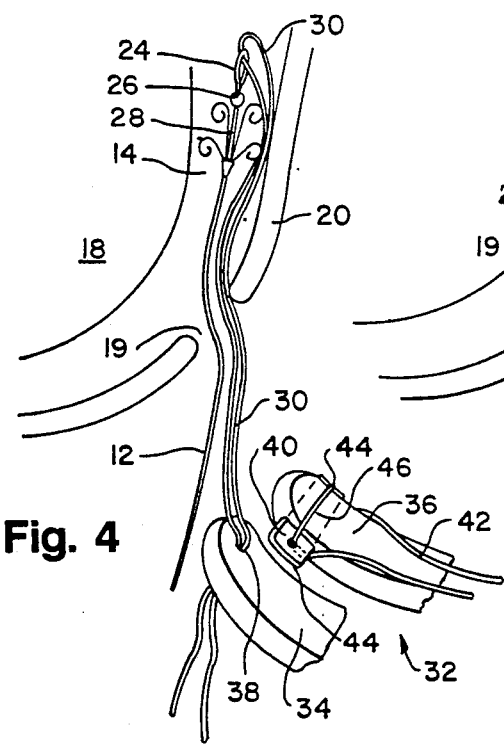

After removal of sheath 16, as shown in FIG. 4 an attachment tool 32, having opposed jaws 34, 36, is brought to bear, first by threading at least one or preferably both of the lengths of cord 30 through an aperture 38 in jaw 34 of the attachment tool.

It can also be seen that the other jaw 36 of the attachment tool carries a plate 40, which plate is held in position on jaw 36 by suture cord 42 which extends typically the distance of attachment tool 32, so that the proximal ends of cord 42 and also well outside of the surgical incision used to gain access to the heart area.

The shape of plate 40 is more clearly shown in FIG. 9, in which plate 40 comprises a central first aperture 41 and a pair of side apertures 44. Cord 42 is shown to extend along the length of jaw 36, then passing underneath plate 40 to project upwardly through one of the side apertures 44. A length 46 of the cord 42 then extends transversely across the side of jaw 36 that is opposed to the side that carries plate 40 in a jaw recess 48 (FIG. 7). The cord 42 then passes downwardly through the other side aperture 44 and then extends rearwardly again along the jaw 36. Thus, plate 40 is temporarily retained in position as long as cord 42 is held under tension.

Figure 5:
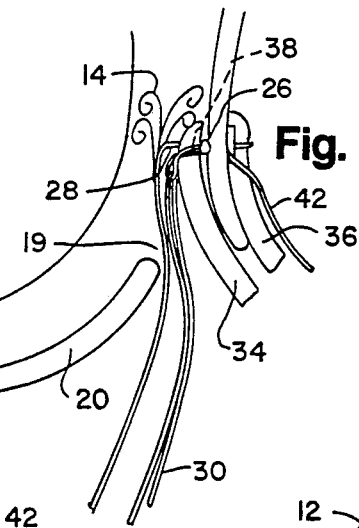

Referring to FIGS. 4 and 5, jaw 34 of the attachment tool is then passed into aperture 19, being guided by the passage of cord 30 through aperture 38 in jaw 34. Eventually, as shown in FIGS. 5, and 7 loop 24 extends through aperture 38, with flexible member 28 extending around the side or end of jaw 34 and bead 26 being seated on aperture 38. Jaws 34, 36 of attachment tool 32 are positioned adjacent an intact portion of the parietal pericardium, spaced from aperture 19 as shown in FIGS. 5 and 7. Plate 40 is shown in FIG. 7 in section, with first aperture 41 being seen in section. A chamber 50 is provided in jaw 36 behind plate 40 and aperture 41.

Then, upon closing of jaws 34, 36, bead 26 may be pressed through aperture 41 in snap-fit relation, with bead 26 fitting into chamber 50, and taking a section of flexible member 28 along with it. Plate 4 is flexible enough, and aperture 41 is sized, to allow this to take place.

Figure 6:
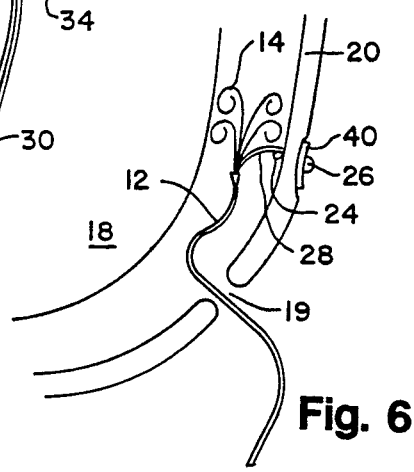

Then, each of cords 30 and 42 are pulled at one distal end to cause the entire cord to be withdrawn from the area of jaws 34, 36 and the attachment tool 32. The attachment tool itself may then be withdrawn from the site, leaving the attached lead 12 in a configuration as shown in FIGS. 6 and 8. Bead 26 is shown to be retained on the side of the parietal pericardium 20 remote from that side facing lead 10 by its snap-fit relation with plate 40. Plate 40 is too large to penetrate through the parietal pericardium 20, even should the stretched portion thereof 52 surrounding bead 26 be broken or necrose.

Thus, flexible member 28 is securely anchored to provide secure anchoring to lead 10. Because of this, outwardly deployed electrodes 14 cannot migrate in an undesirable manner, so that a second lead may be positioned at a different but relatively close area of the heart, with good reliance that the respective electrodes of the two leads will never touch.

As an advantage of the method of this invention, before affixation of the lead, it is possible to move the lead around to test defibrillation thresholds until a desirable defibrillation threshold is obtained. Only then, if desired, can the steps illustrated in FIGS. 4 through 8 be performed so that each lead which is implanted in accordance with this invention can be implanted with a high probability of effective performance.

Then, the aperture 19 in parietal pericardium 20 may be sutured together to close the aperture down around lead 10 on all sides.

Thus, a method is provided in which a lead may be implanted at a desired position at the heart without need of visually observing the deployed electrodes 14 and without seeing the exact attachment site of the lead.

FIGS. 10 and 11 show two particular types of attachment tools which may be used in accordance with this invention. The attachment tools may be of the generally conventional design of analogous surgical instruments except for the precise shapes of their jaws, which may be as shown in FIG. 7, and as otherwise indicated in here.

As a specific, different modification, each of the respective jaws 34, 36 of FIG. 10 may carry tunnel means to position and house a portion of the respective cords carried on the jaw and arm of the tool. For example, jaw 36 of tool 54 defines tunnel members 56 through which cord 42 can extend, to hold the cord in a position essentially parallel to the extent of jaw 36 and the corresponding tool arm 36a.

Likewise, jaw 34 may carry one or more tunnel members 60 for the same purpose, positioned along jaw 34 and in its corresponding arm 34a for control and retention of cord 30.

The attachment tool illustrated in FIG. 10 is particularly adapted for emplacing leads at anterior heart positions.

Turning to FIG. 11, a similar emplacement tool is shown which may function in a manner similar to that of the previous disclosure. Specifically, the tool of FIG. 11 is adapted for emplacement of leads at posterior heart positions. Apart from the difference in shape of the tool in FIG. 11, it may function in a manner similar to the tool of FIG. 10. Specifically, tunnel members 56a and 60a may be provided for the retention of the respective cords which are present for purposes described above.

Referring to FIG. 12, an alternate embodiment of attachment tool in accordance with this invention is shown, in the process of attaching a lead with a different retention system.

As before, the parietal pericardium 62 of the patient's heart 64 is opened with an aperture 66, so that one jaw 67 of an attachment tool 68 may be inserted. Another jaw 70 is positioned on the outside of the parietal pericardium, and each of the jaws carries an interengaging part 72, 74 of a fastener member.

As specifically shown in FIG. 13, part 74 of the fastener member may comprise a ring which defines a plurality of prongs 76, while part 72 of the fastener member defines another ring with a facing annular groove 78. To make connection, the prongs of ring 77 fit into the groove 78 of ring 79, and are retained there, in the manner rather of the assembly of a clothing snap on a piece of cloth, with the design being similar to such a conventional clothing snap.

As shown in FIG. 12, lead 78 is carried in a sleeve 80, which may be withdrawn to cause the electrodes at the distal end of lead 78 to expand outwardly in the conventional manner of a deployable lead having one or more electrodes. The distal end of lead 78 is connected to one end of a flexible member 82 such as a strong, permanent surgical suture or the like, while the other end of flexible member 82 is connected to fastener half 72.

Thus, the structure as illustrated in FIGS. 12 and 13 is analogous to the previous embodiment, except that lead 7 is being emplaced outside of the parietal pericardium 62 rather than the inside thereof. When the two jaws are brought together by handle mechanism 84, with the parietal pericardium between them, the fastener member halves 72, 74 are connected together in a permanent manner, if desired, and lead 78 is thus permanently attached in a desired position relative to the heart.

Sleeve 80 is withdrawn to deploy the electrodes of the lead, and tool 68 is correspondingly withdrawn, leaving lead 78 behind. Aperture 66 in the parietal pericardium is sutured, and the patient is closed up.

Referring to FIG. 15, another method of securing of a lead 110 having a distal patch-type electrode 112 to the parietal pericardium 114 is shown. An attachment tool having a pivotally mounted pair of jaws 116, 118 is shown in which the distal end portion of jaw 116 penetrates a hole 120 which has been cut in the parietal pericardium. The distal end of jaw 116 carries a snap-type fastener member 122, as previously described, for engagement with a snap fastener member 124 which is attached to electrode 112. Particularly, snap fastener member 124 may be attached to the woven metal fabric of the patch electrode 112 by conventional gluing, welding or the like. Thus, with a single closing motion, the respective jaws 116, 118, can press snap fasteners 122, 124 together into snap-fit relation, to cause the securance of patch electrode 112 to the parietal pericardium. It can be seen in this particular embodiment that jaw 118 does not carry an attachment member part, but is merely present to provide pressure.

Referring to FIG. 16, jaws 116a, 118a of a similar attachment tool carry at their respective distal ends a pair of snap fasteners 122a, 124a similar to the previous embodiment, with jaw 116a penetrating through hole 120 to be on the inside of the parietal pericardium 114a. Jaws 116a and 118a may then be closed to cause snap fasteners 122a, 124a to be brought together into snap-fit relation on the parietal pericardium as in previous embodiments. See for example FIG. 12, with the difference that no electrode or lead is attached to either of snap-fasteners 122a, 124a.

Snap-fastener 122a may be temporarily attached to jaw 116a by a projection 126 carried by fastener 122a and extending into a mating recess of jaws 116a. Similarly, fastener half 124a may be releasably carried on jaw 118a by a second projection 128 which matingly fits into a corresponding recess in jaw 118a. Conversely, the jaws may carry the projections and the fasteners the recesses, to the same effect.

Projections 126, 128 and the corresponding recesses may be so shaped that when the respective snap fasteners 122a, 124a are brought together into snap-fit relation, the force required to cause projections 126, 128 to be pulled out of their recesses in jaws 116a, 118a is less than the force required to separate the respective snap halves 122a, 124a from each other. Thus, after the snap halves 122a, 124a are brought together into locked relationship to form a complete snap 130 connector carried on the parietal pericardium 114a (as in FIG. 17), jaws 116a, 118a may be brought apart again, causing spontaneous separation of projections 126, 128 from their recesses. Then, jaws 116a, 118a may be removed, if desired, until the subsequent step of FIG. 17 is to be performed. Such projections can be used with the other embodiments as well.

Referring to FIG. 17, a lead 110a and a connected, distal patch electrode 112a are attached to snap connector 130.

Patch electrode 112a is shown to carry a third snap connector 124b, which fits with projection 128 of snap connector 130. Specifically, the overall design of such a snap system may resemble the well-known clothing snaps, in which each mating snap on a separate piece of fabric to be snapped together is made of a pair of interlocked snaps. One of such a snap pair is analogous to snap portions 122a, 124a. A third snap member 124b then may lack a mating snap section, but may be attached to the patch electrode in the manner of snap 124 of FIG. 15, and which snaps into engagement with the pair of engaged snaps 130. This process is facilitated once again by jaws 116a, 118a which press third snap 124b into snapping engagement with the combined snaps 130, which comprise snap portions 122a and 124a.

As another embodiment, FIG. 18 shows a lead 110b, having a patch electrode 110c and a distal tab member 134, which carries a connector part 136, capable of reversible snap-fit connection with attachment member 130, which is carried on the parietal pericardium 114a, as shown in FIG. 17.

FIG. 19 shows an alternate jaw 118b of an attachment tool, which otherwise may be similar to that shown previously. Jaw 118b defines parallel, axial slots 140, open at the distal ends 142. An attachment member part 124c can thus be retained in sliding relation. Accordingly, attachment member part 124c can be positioned by jaw 118b of the attachment tool to engage with another, mating attachment member, with attachment member 124c defining either an aperture or a projection as may be desired.

Then, after member 124c is mated with another attachment member on the opposite side of the parietal pericardium as in previous embodiments, it may be freed from its engagement with jaw 118b by simply drawing jaw 118b proximally away, to cause member 124c to slide out of distal end 142 of the respective slots 140, out of engagement with jaw 118b. Thus, attachment member 124c, and a lead or tether 144 to which it is optionally attached, may be implanted. Also slots 140, 142 may carry any type of appropriate attachment member.

FIGS. 20 and 21 show a jaw 116b of an attachment tool which may be used in conjunction with jaw 118b of the same tool, if desired. Jaw 116b is adapted to carry generally a spherical bead 146 in a slot 148, with bead 146 being attached to a tether or cord 150. Bead 146 or any modification thereof may comprise part of an attachment member which can engage with apertured attachment member 124c, to be retained on the parietal pericardium in a manner similar to that specifically illustrated in FIGS. 7-8.

Then, when attached, jaw 116b may be disengaged simply by sliding the attachment tool proximally away, so that cord 150 slides distally out the free end of slot 148, typically simultaneously as attachment member 124c slides out of its respective slots 140.

Figure 22:
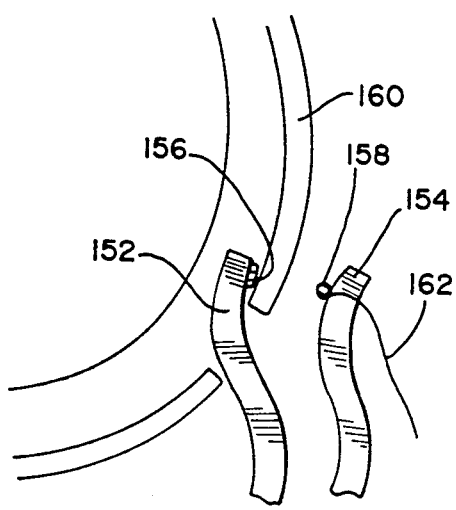
FIG. 22 is a schematic view showing the jaws of an attachment tool carrying a ball and apertured plate-type attachment member part, about to be attached to the parietal pericardium of the patient.

Referring to FIG. 22 a step of another embodiment of this invention is shown, in which the jaws 152, 154 of an attachment tool are used as in previous embodiments to place attachment member parts 156, 158 onto the parietal pericardium 160. The attachment member which comprises parts 156, 158 may be of the spherical bead and apertured plate type, as shown in previous embodiments. Spherical bead 158 carries a tether or cord 162, with tether 162 extending from bead 158 back along the attachment tool and through an access site of the body of the patient.

Figure 23:
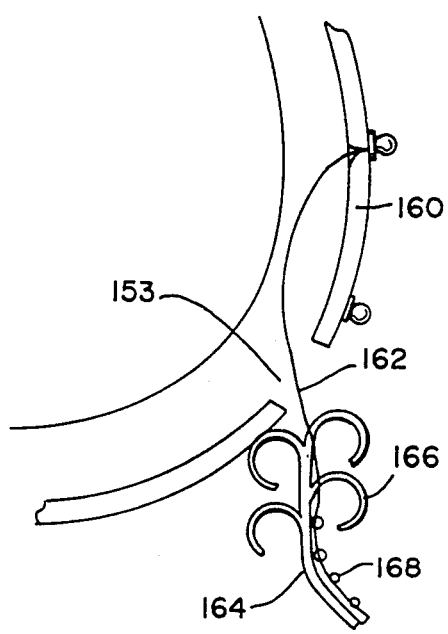
FIG. 23 is a schematic view of a subsequent method step from that of FIG. 22 in which the attachment tool is withdrawn, and a lead is advanced along the tether carried by the ball-type attachment member part so that the distal electrode of the lead may be spontaneously advanced into position against the parietal pericardium.

Then, as shown in FIG. 23, a lead 164 having multiple, arcuate electrodes 166, is slidingly connected to tether 162 by means of laterally positioned rings 168 through which tether 162 extends. Catheter 164 may then be advanced along tether 162, in the manner shown, or, if desired, in a tubular sleeve to straighten out the respective electrodes 166 until after implantation at the proper position, after which the sleeve may be withdrawn and the electrodes 166 allowed to spring outwardly. Lead 164 is guided to the proper position, with tether 162 functioning rather like a guidewire for an angiography or an angioplasty catheter. This may be applied to other lead designs as well.

Figure 24:
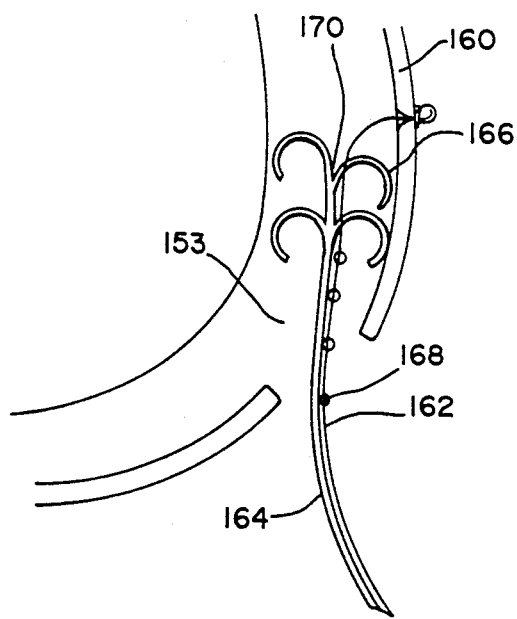
FIG. 24 shows a further step in the process illustrated by FIGS. 22-23.

Lead 164 can be advanced along tether 162 to a position of substantially maximum advancement as shown in FIG. 24, in which the distal end 170 and electrodes 166 are positioned within the parietal pericardium 160, entering through aperture 153. Tether 162 can retain catheter 164 in the desired position for an indefinite period of time. Also, lead 164 may be sutured to the parietal pericardium adjacent aperture 153.

Figure 25:
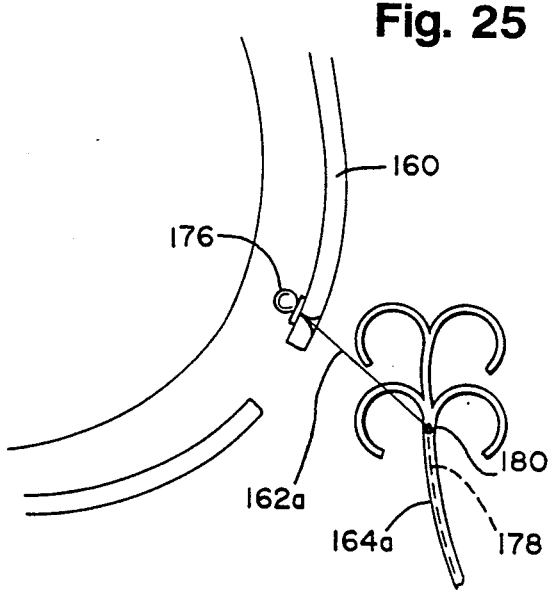
FIG. 25 shows a schematic view of a similar process in which the orientation of the attachment member is reversed so that a lead can be advanced along the tether into engagement with the outer surface of the parietal pericardium.

Referring to FIG. 25, a similar process can be performed, in which an attachment member 176, comprising a mating bead and apertured plate in a manner similar to previous embodiment, can be mounted on the parietal pericardium 160 in the opposite direction from that shown in the embodiment of FIGS. 22-24. Tether 162a extends outwardly from the parietal pericardium 160 rather than inwardly as in the previous figures. Thus, bead 164a may be advanced along tether 162a to occupy a position closely adjacent to the exterior of the parietal pericardium rather than the interior thereof.

Also, in this embodiment, lead 164a may define an internal lumen 178 and a side aperture 180 through which tether 162a may extend, so that as lead 164a is advanced along tether 162a, at least a portion of the tether occupies the internal lumen 178 rather than rings 168 as in the previous embodiment.

If desired, the leads of this invention which are placed may be replaced by catheters, or liquid transmitting leads rather than electrical impulse transmitting leads, in any circumstance where such a device is to be positioned and retained next to a body membrane which is strong enough to carry an attachment member. The parietal pericardium is made of dense fibrous connective tissue, and is thus strong, and capable of retaining any of various designs of attachment members, including the designs shown herein.

Thus, by this means and also by the previous embodiment, it is possible to implant one or more leads at a position about the heart or elsewhere, remote from the site of the surgery, well beyond where suturing can take place. Significant advantages of the method of implantation described above may also be achieved by this embodiment of the invention as well as by the previous embodiment.

Turning to FIG. 14, the distal end of a lead 90 is shown, terminating in a conventional paddle electrode 92 formed of a mesh of conductive wires and surrounded by a supporting cuff 94 which contains a suturable fabric, rubber, or the like.

A member 96 is provided for securing an attachment loop and a fastener onto a lead. Member 96 may be used with respect to paddle electrode lead 90 or a deployable lead as disclosed in this application, or any other appropriate type of lead.

Member 96 carries a needle 98 which may be used for suturing. A suture 100 or equivalent cord is connected to the end of the needle, and is of sufficient length to permit suturing or attachment thereof by means of needle 98 to suture rim 94 or to any other appropriate spot on typically the distal end of a deployable or other type of lead.

At the end of cord 100 opposed to needle 98, an attachment bead 102 is provided, or any other desired attachment member. Attachment bead 102 may be used in the manner previously described with respect to attachment bead 26.

Then, cord loop 104 is also provided, which cord loop is intended for use in the manner of loop 24 as previously discussed.

Accordingly, an attachment bead 102 and a cord loop 104 may be attached to a large variety of leads by simple sewing action, making use of cord 100 and needle 98. Then, when cord 100 has been firmly attached to the lead, needle 98 may be cut away, to prepare any desired lead for use in accordance with this invention.

The above has been offered for illustrative purposes only and is not intended to limit the scope of the invention of this application, which is as defined in the claims below.

That which is claimed is:

1. A method of implanting in the body an implantable member, which comprises:
inserting a first of a pair of pivotally attached jaws of an attachment tool through a hole in a tissue membrane while placing the other of said pivotally attached jaws outside of the tissue membrane in a position of registry with the first of said jaws, said jaws carrying an attachment member which is attached to said implantable member and is adapted for securance to the tissue membrane; and bringing said jaws together in pressing relation, with the tissue membrane and the attachment member positioned between said jaws, to cause attachment of said attachment member to the tissue membrane for securance of said implantable member thereto; and disconnecting said jaws from the attachment member and said implantable member.

2. The method of claim 1 in which each of said jaws carries an interconnecting portion of said attachment member, each interconnecting portion being proportioned for mating engagement with the other portion upon the application of pressure of said jaws with said interconnecting portions and the tissue membrane positioned between said jaws.

3. The method of claim 1 in which said implantable member is a lead, said lead being attached to the attachment member at a position outside of the parietal pericardium.

4. A method of implanting in the body an implantable member, which comprises:
inserting one of a pair of pivotally attached jaws of an attachment tool through a hole in a tissue membrane, while placing the other of said pivotally related jaws outside of the tissue membrane in a position of registry with the first of said jaws, said jaws carrying an attachment member which is to be attached for securance to said tissue membrane; and bringing said jaws together in pressing relation, with the tissue membrane and the attachment member positioned between said jaws, to cause attachment of said attachment member to the tissue membrane; and thereafter attaching said implantable member to said attachment member and disconnecting said jaws from the attachment member.

5. The method of claim 4 in which said implantable member is a lead which defines a distal electrode that carries means for securing said lead to said attachment member.

6. The method of claim 5 in which said securing means is carried on a flexible tab carried on said electrode.

7. A method of claim 5 in which said electrode comprises a flexible patch, said means for securing being carried on said patch.

8. A method of implanting a lead at the heart, the improvement comprising:
inserting a first of a pair of pivotally attached jaws of an attachment tool through a hole in the parietal pericardium surrounding the pericardial cavity, while placing an opposed one of said pivotally related jaws outside of the parietal pericardium in a position of registry with the first of said jaws, and further comprising implanting said lead at the heart including the step of bringing said jaws together in pressing relation with the parietal pericardium positioned between said jaws, to cause attachment of an attachment member to the parietal pericardium, and thereafter withdrawing said jaws.

9. The method of claim 8 in which, after said attachment member is attached to the parietal pericardium, an electrode carried by said lead is attached to said attachment member.

10. The method of claim 8 in which, after attachment of said attachment member to the parietal pericardium, a connection member which is attached to said lead is releasably attached to said attachment member.

11. The method of claim 8 in which said attachment member comprises two interlocking halves which are brought together by said closing of said jaws with the parietal pericardium positioned between said halves, one of said halves being attached to said lead.

12. The method of claim 11 in which said interlocking attachment member halves are each releasably seated respectively in a longitudinal slot defined in said first and opposed jaws, whereby said halves are retained by said slots against motion transverse of said jaws.

13. A method of implanting a lead in the body, which comprises:
inserting an attachment member connected to tether means through an access site into the body; attaching said attachment member to a tissue membrane, while said tether means extends from the attachment member through the access site; and sliding a lead along the tether member, beginning at the access site, through the patient to cause a distal end of said lead to occupy a position adjacent to the attachment member.

14. The method of claim 13 in which said lead is attached in a position with its distal end adjacent the parietal pericardium.

15. The method of claim 13 in which said lead is tubular, said tether means occupying the lumen of said lead as the lead is advanced to a position where the distal end of the lead is adjacent the attachment member.

16. The method of claim 13 in which said lead defines loop segments through which said tether means extends to facilitate advancement of said lead along the tether means to a position with a lead distal end being adjacent the attachment member.

* * * * *